United States Patent
Reddy et al.

(10) Patent No.: US 8,000,810 B2
(45) Date of Patent: Aug. 16, 2011

(54) SYSTEMS AND METHODS FOR TRANSVENOUS LEAD IMPLANTATION

(75) Inventors: G. Shantanu Reddy, Minneapolis, MN (US); Shrojalkumar M. Desai, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1157 days.

(21) Appl. No.: 11/688,699

(22) Filed: Mar. 20, 2007

(65) Prior Publication Data
US 2008/0234792 A1    Sep. 25, 2008

(51) Int. Cl.
*A61N 1/05* (2006.01)
(52) U.S. Cl. .................. 607/126; 607/121
(58) Field of Classification Search .......... 607/115–116, 607/119–126
See application file for complete search history.

(56) References Cited

U.S. PATENT DOCUMENTS

| | | |
|---|---|---|
| 4,819,661 A | 4/1989 | Heil, Jr. et al. |
| 4,827,940 A | 5/1989 | Mayer et al. |
| 5,091,204 A | 2/1992 | Ratner et al. |
| 5,091,214 A | 2/1992 | Muller et al. |
| 5,221,261 A | 6/1993 | Termin et al. |
| 5,224,491 A | 7/1993 | Mehra |
| 5,449,372 A | 9/1995 | Schmaltz et al. |
| 5,514,174 A | 5/1996 | Heil, Jr. et al. |
| 5,531,779 A | 7/1996 | Dahl et al. |
| 5,649,906 A | 7/1997 | Gory et al. |
| 5,679,659 A | 10/1997 | Verhoeven et al. |
| 5,755,762 A | 5/1998 | Bush |
| 5,871,531 A | 2/1999 | Struble |
| 5,902,331 A | 5/1999 | Bonner et al. |
| 5,951,597 A | 9/1999 | Westlund et al. |
| 5,954,761 A | 9/1999 | Machek et al. |
| 6,129,750 A | 10/2000 | Tockman et al. |
| 6,136,021 A | 10/2000 | Tockman et al. |
| 6,161,029 A | 12/2000 | Spreigl et al. |
| 6,178,356 B1 | 1/2001 | Chastain et al. |
| 6,304,786 B1 | 10/2001 | Heil, Jr. et al. |
| 6,397,109 B1 | 5/2002 | Cammilli et al. |
| 6,408,214 B1 | 6/2002 | Williams et al. |
| 6,510,347 B2 | 1/2003 | Borkan |

(Continued)

FOREIGN PATENT DOCUMENTS

EP     0795343 A2     9/1997

(Continued)

OTHER PUBLICATIONS

Park et al., "Bacterial adhesion on PEG modified polyurethane surfaces," Biomaterials, vol. 19, pp. 851-859, 1998.

(Continued)

*Primary Examiner* — Carl H Layno
*Assistant Examiner* — Jessica Sarcione
(74) *Attorney, Agent, or Firm* — Faegre & Benson LLP (57) ABSTRACT

Some embodiments relate to a method of implanting a cardiac lead. An expansion module is implanted in a target region within vasculature, the target region being defined by a portion of a brachiocephalic vein and a portion of a corresponding subclavian vein. The expansion module is transitioned from a collapsed state to an expanded state within the target region to contact the vasculature. A cardiac lead is implanted through the expansion module, the cardiac lead defining an intermediate section corresponding to the target region. The intermediate section of the cardiac lead includes a surface treatment adapted to reduce at least one of cell proliferation, thrombosis, fibrosis, and inflammation at the target region.

9 Claims, 6 Drawing Sheets

U.S. PATENT DOCUMENTS

| | | |
|---|---|---|
| 6,709,415 B2 | 3/2004 | Navia et al. |
| 6,711,443 B2 | 3/2004 | Osypka |
| 6,730,064 B2 | 5/2004 | Ragheb et al. |
| 6,774,278 B1 | 8/2004 | Ragheb et al. |
| 6,842,648 B2 | 1/2005 | Partridge et al. |
| 2002/0026228 A1 | 2/2002 | Schauerte |
| 2002/0045926 A1 | 4/2002 | Heil, Jr. et al. |
| 2002/0082679 A1 | 6/2002 | Sirhan et al. |
| 2002/0103522 A1 | 8/2002 | Swoyer et al. |
| 2003/0065374 A1 | 4/2003 | Honeck |
| 2003/0083646 A1 | 5/2003 | Sirhan et al. |
| 2003/0139801 A1 | 7/2003 | Sirhan et al. |
| 2003/0144727 A1 | 7/2003 | Rosenthal et al. |
| 2003/0163184 A1 | 8/2003 | Scheiner et al. |
| 2003/0199961 A1 | 10/2003 | Bjorklund et al. |
| 2003/0204231 A1 | 10/2003 | Hine et al. |
| 2003/0220677 A1 | 11/2003 | Doan et al. |
| 2004/0059404 A1 | 3/2004 | Bjorklund et al. |
| 2004/0062852 A1 | 4/2004 | Schroeder et al. |
| 2005/0070985 A1 | 3/2005 | Knapp et al. |
| 2005/0080472 A1 | 4/2005 | Atkinson et al. |
| 2005/0131511 A1 | 6/2005 | Westlund |
| 2005/0137669 A1* | 6/2005 | Krishnan et al. ............. 607/122 |
| 2006/0241737 A1 | 10/2006 | Tockman et al. |

FOREIGN PATENT DOCUMENTS

| | | |
|---|---|---|
| WO | 03092799 A1 | 11/2003 |
| WO | 2004012874 A1 | 2/2004 |
| WO | 2004060478 A1 | 7/2004 |
| WO | 2005051229 A2 | 6/2005 |

OTHER PUBLICATIONS

Ruardij et al., "Adhesion and Patterning of Cortical Neurons on Polyethylenimine- and Flourocarbon-Coated Surfaces," IEEE Transactions on Biomedical Engineering, vol. 47, No. 12, pp. 1593-1599, Dec. 2000.

Yuan et al., "Reduced Platelet Adhesion on the Surface of Polyurethane Bearing Structure of Sulfobetaine," Journal of Biomaterials Applications, vol. 18, pp. 123-135, Oct. 2003.

Bae et al., "Synthesis and characterization of heparinized polyurethanes using plasma glow discharge," Biomaterials, vol. 20, pp. 529-537, 1999.

Feng et al., "Protein resistant surfaces: Comparison of acrylate graft polymers bearing oligo-ethylene oxide and phosphorylcholine side chains," Biointerphases, vol. 1, No. 1, pp. 50-60, Mar. 2006.

Bar-Cohen et al., "Age, Size, and Lead Factors Alone Do Not Predict Venous Obstruction in Children and Young Adults with Transvenous Lead Systems," J Cardiovasc Electrophysiol, vol. 17, No. 7, pp. 754-759, Jul. 2006.

Bracke et al., "Venous Occlusion of the Access Vein in Patients Referred for Lead Extraction: Influence of Patient and Lead Characteristics," PACE, vol. 26, pp. 1649-1652, Aug. 2003.

Oginosawa et al., "Prevalence of Venous Anatomic Variants and Occlusion Among Patients Undergoing Implantation of Transvenous Leads," PACE, vol. 28, pp. 425-428, May 2005.

Oginosawa et al., "The Incidence and Risk Factors for Venous Obstruction After Implantation of Transvenous Pacing Leads," PACE, vol. 25, No. 11, pp. 1605-1611, Nov. 2002.

* cited by examiner

SYSTEMS AND METHODS FOR TRANSVENOUS LEAD IMPLANTATION

TECHNICAL FIELD

The present invention relates to medical systems and methods for transvenous lead implantation. More specifically, the invention relates to venous occlusion and lead attachment associated with transvenously implanted leads.

BACKGROUND

Various medical devices interact with leads to assist with sensing, stimulating, or other functionality. For example, some implantable medical devices for treating irregular heart contractions, such as defibrillators and pacemakers, utilize transvenous leads for electrically stimulating the heart or for related sensing functions. According to some methods of transvenous lead implantation, one or more leads are introduced into a patient's vasculature at a venous access site. The leads are then deployed through the vasculature to a deployment site, for example in or near the heart.

Transvenous leads can contribute to partial or complete venous occlusion of the vasculature through which the leads are deployed. In fact, some evidence suggests that significant venous occlusion occurs in more than about 25% of patients. This interference with normal blood flow is undesirable, as it may result in arm pain and swelling, among other health problems. Occlusions also interfere with one or more of the ability to repair, add, remove, or replace leads. Furthermore, the presence of leads interferes with remedial measures for treating occlusions, such as the use of balloon catheters.

SUMMARY

Some embodiments relate to a method of implanting a cardiac lead. An expansion module is implanted in a target region within vasculature, the target region being defined by a portion of a brachiocephalic vein and a portion of a corresponding subclavian vein. The expansion module is transitioned from a collapsed state to an expanded state within the target region to contact the vasculature. A cardiac lead is implanted through the expansion module, the cardiac lead defining an intermediate section corresponding to the target region. The intermediate section of the cardiac lead includes a surface treatment adapted to reduce at least one of cell proliferation, thrombosis, fibrosis, and inflammation at the target region.

Other embodiments relate to a cardiac lead system for implantation in a venous pathway from an IMD to a patient's heart, the pathway including a target region defined by a portion of a brachiocephalic adjacent to an external jugular vein and a portion of a corresponding subclavian vein adjacent to the external jugular vein. The cardiac lead system includes a cardiac lead and an expansion module. The cardiac lead extends between a terminal end for connection to an implantable medical device and a working end adapted for at least one of sensing and stimulating. The cardiac lead defines a proximal section, a distal section, and an intermediate section between the proximal and distal sections. The cardiac lead is adapted such that the intermediate section extends through the target region upon implantation of the cardiac lead. The intermediate section of the cardiac lead includes a surface treatment for reducing venous occlusion at the target region. The expansion module includes a first expansion member. The first expansion member is adapted to expand in diameter from a collapsed state to an expanded state to contact and mechanically support a vessel wall in the target region and to slidably receive the intermediate section in the expanded state.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
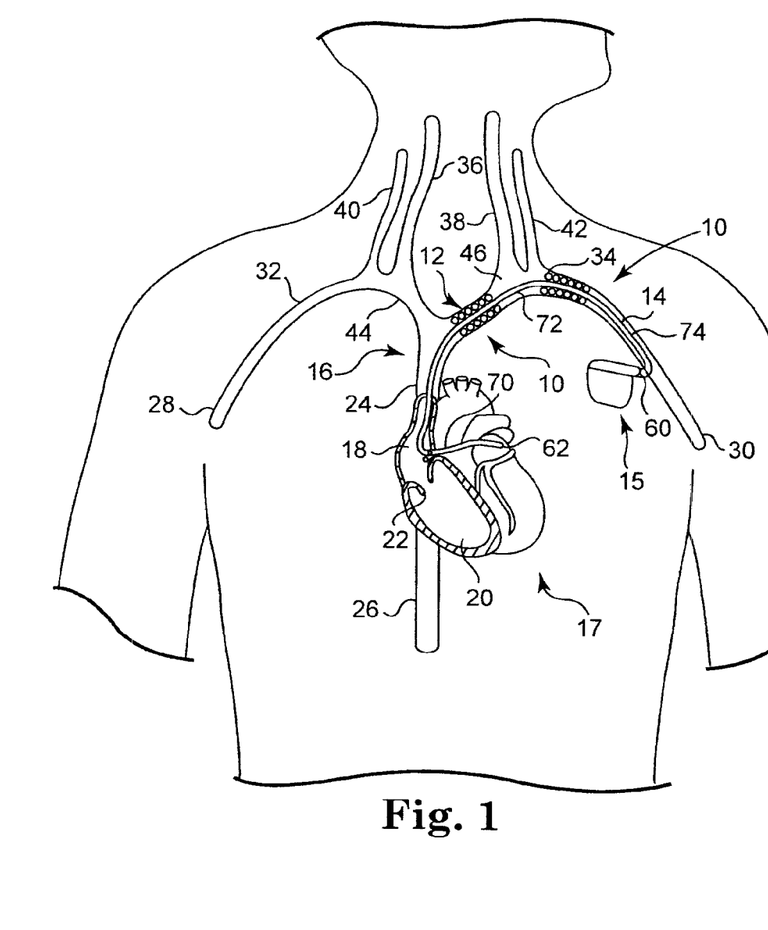
FIG. 1 shows a cardiac lead system in a body according to an exemplary embodiment.

FIG. 1 shows a cardiac lead system 10 including an expansion module 12 and a cardiac lead 14 connected to an implanted medical device (IMD) 15, such as a cardiac rhythm management (CRM) device. In some embodiments, the cardiac lead 14 is deployed to extend from the IMD 15 through a vascular pathway 16, terminating at a location proximate a patient's heart 17.

Methods and devices for deploying the cardiac lead 14 within the vascular pathway 16, as well as additional features of the system 10 are subsequently described in greater detail. By way of background, the heart 17 includes the right atrium 18 and the right ventricle 20 which are separated by the tricuspid valve 22. During normal operation of the heart 17, deoxygenated blood is fed into the right atrium 18 through the superior vena cava 24 and the inferior vena cava 26. The major veins supplying blood to the superior vena cava 24 include the right and left axillary veins 28, 30, which flow into corresponding right and left subclavian veins 32, 34. The right and left external jugular veins 36, 38, along with the right and left internal jugular veins 40, 42, join the right and left subclavian veins 32, 34 at a junction to form corresponding right and left brachiocephalic veins 44, 46, respectively. The right and left brachiocephalic veins 44, 46, also described as the innominate veins, combine to flow into the superior vena cava 24.

As shown in FIG. 1, the vascular pathway 16 initiates on the left side of the body and includes the left subclavian vein 34, the left brachiocephalic vein 46, and the superior vena cava 24. According to various exemplary embodiments, the cardiac lead 14 enters from any of the left axillary vein 30, the left subclavian vein 34, and the left external jugular 38. The cardiac lead 14 travels through the left brachiocephalic vein 46 and the superior vena cava 24 into the right atrium 18. The cardiac lead 14 then extends through the coronary sinus ostium so that the cardiac lead 14 is located in the coronary sinus. In some cases, the cardiac lead 14 then travels further into a coronary sinus branch vessel so that a distal tip of the lead 14 is finally disposed generally adjacent the left ventricle. Although the following description generally addresses embodiments in relation to the left side of the body, it should be understood that this description is cumulative in nature, with similar principles applying to the right side of the body. For example, according to one exemplary embodiment, the vascular pathway 16 optionally initiates on the right side of the body with the vascular pathway 16 including corresponding vasculatures on the right side of the body.

Figure 2:
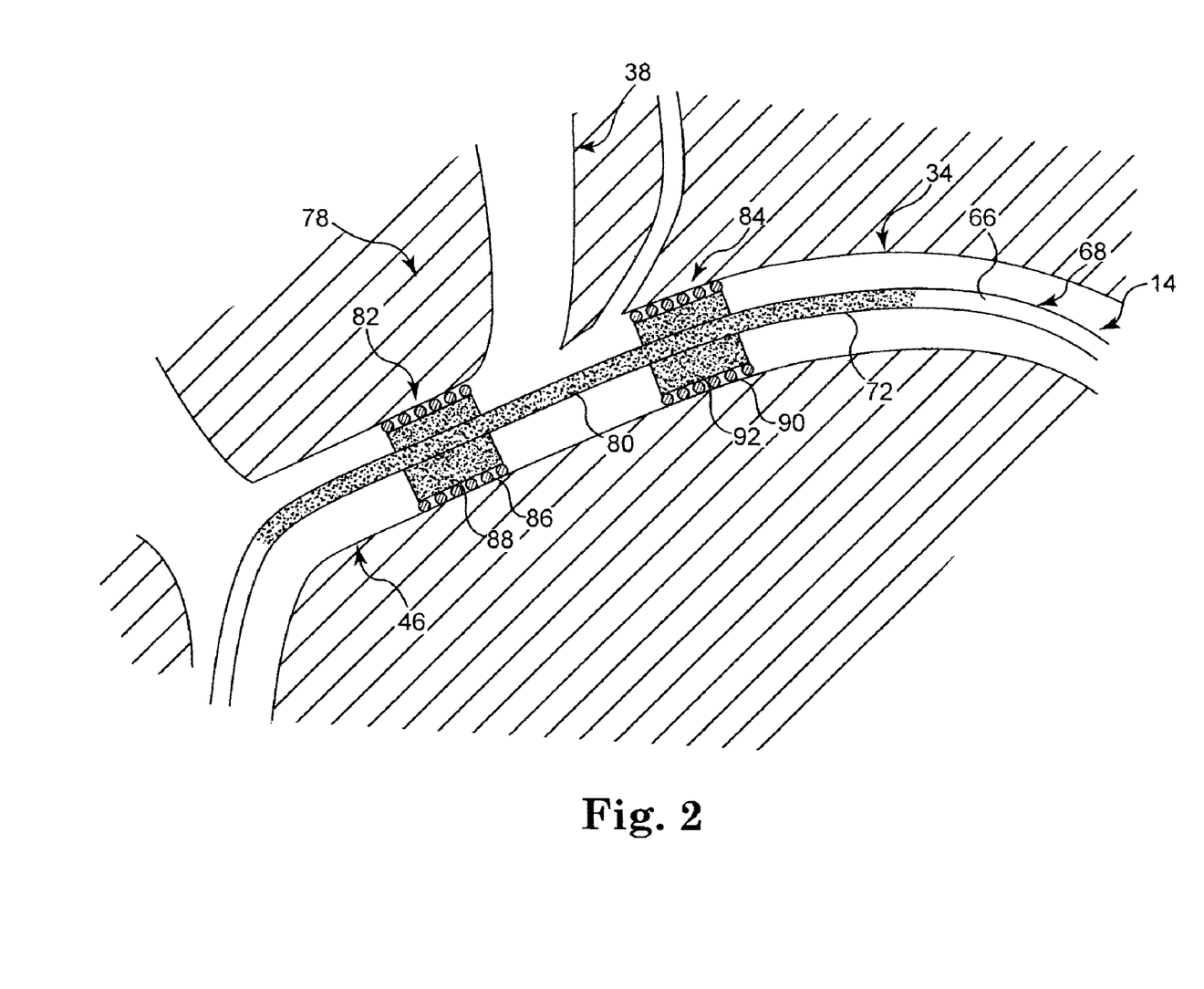
FIG. 2 shows an enlarged view of the cardiac lead system of FIG. 1 extending through a target region.

In one exemplary embodiment, the cardiac lead 14 extends between a terminal end 60 adapted for connection to the IMD 15 and a working end 62 adapted for at least one of stimulating the heart 17, sensing one or more physiologic parameters, or other stimulating or sensing functions, for example. Generally, the cardiac lead 14 includes an insulator 66 (FIG. 2) and defines an internal conductive pathway (not shown) for communicating various types of signals and an outer surface 68 (FIG. 2). The cardiac lead 14 also defines a distal section 70, an intermediate section 72, and a proximal section 74.

The insulator 66 (FIG. 2) includes a non-conductive material component. In some embodiments, the internal conductive pathway of the cardiac lead 14 is electrically conductive while the insulator 66 includes an electrically insulative material, although other types of conductors, light or sound conductors, for example, as well as corresponding insulative materials are also contemplated. Generally, the insulator 66 is substantially tube- or sheath-shaped and extends along a substantial portion of the cardiac lead 14. The insulator 66 is optionally formed as a single layer or includes multiple layers. In some embodiments, the insulator 66 is formed of a material including one or more of polyurethane (PU), silicone (PDMS), SIBS, expanded polytetrafluoroethylene (ePTFE), biocompatible metals, such as nickel-titanium alloy (NiTi), or other biocompatible materials. In some embodiments, the insulator forms the outer surface 68. If desired, the insulator 66 includes a jacket or additional layer of material positioned at one or more of the sections 70, 72, 74, thereby defining that portion of the outer surface 68.

In some embodiments, the cardiac lead 14 is adapted or otherwise sized and shaped such that, upon transvenous implantation of the cardiac lead 14, the distal section 70 corresponds to the portion of the vascular pathway 16 including the superior vena cava 24 and the heart 17, for example, while the proximal section 74 corresponds to the portion of the vascular pathway 16 corresponding to the left axillary vein 30.

FIG. 2 shows an enlarged view of a target region 78 where the left subclavian vein 34 and the left external jugular vein 38 meet at a junction to form the left brachiocephalic vein 46. In particular, the target region 78 includes a portion of the left brachiocephalic vein 46 adjacent the left external jugular vein 38 and a portion of the left subclavian vein 34 adjacent to the left external jugular vein 38. With reference to FIG. 2, the cardiac lead 14 is adapted, or otherwise sized and shaped such that, upon transvenous implantation of the cardiac lead 14, the intermediate section 72 generally extends through or otherwise corresponds to the target region 78 according to some embodiments.

The target region 78 is susceptible to clotting and other sources of venous occlusion following transvenous implantation of leads (such as the cardiac lead 14) through the target region 78. Potential causes of venous occlusion in the target region 78 include one or more of cellular adhesion onto the cardiac lead 14, blood flow stasis at the target region 78, and stenosis from lead-vein wall mechanical interaction at the target region 78. Although some embodiments are adapted to address occlusion mechanisms at the target region 78 in particular, in other embodiments the cardiac lead 14 is adapted to reduce venous occlusion at any number of target regions along the vascular pathway 16, including along a substantial entirety thereof.

According to these embodiments, the intermediate section 72 corresponding to the target region 78 is adapted for at least one of substantially interfering with clot formation, blood cell or other cellular adhesion to the cardiac lead 14, protein adsorption, platelet activation, thrombosis, mechanical irritation of vessel walls following transvenous implantation, or other mechanisms contributing to venous occlusion. For example, the intermediate section 72 of the cardiac lead 14 and in particular the outer surface 68, is provided with a surface treatment 80 including one or more eluting or non-eluting coatings or surface modifications to provide at least one of antiproliferative, antithrombogenic, anti-inflammatory, and anti-fibrosis performance. For example, a non-eluting surface modification of phosphorylcholine, taurine, and/or sulfobetaine is employed as desired.

In some embodiments, the intermediate section 72 in particular is selected for the surface treatment 80 in order to target reduction of venous occlusion at the target region 78. Furthermore, the intermediate section 72 optionally includes an additional jacket of material (not shown) having the surface treatment 80. In some embodiments, other portions of the cardiac lead 14 additionally or alternatively include similar surface treatments and features. For example, substantially all of the outer surface 68 is provided with the surface treatment 80 to promote reduced venous occlusion.

In some embodiments, the outer surface 68 includes a biocompatible polymer and/or metal material, for example, and the surface treatment 80 includes a PEG surface modification via grafting of PEG to the outer surface 68 to provide blood compatibility. For example, a chloro- or acetoxy-silane is optionally immobilized on the outer surface 68 followed by plasma treatment to generate peroxides on the material. PEG acrylate/methacrylate is then coated onto the outer surface 68 which is followed by UV treatment to initiate free radical grafting of PEG onto the outer surface 68.

In some embodiments, the outer surface 68 includes SIBS, PDMS, and/or PU material, for example, and the surface treatment 80 includes an ethylene-glycol surface modification to limit at least one of protein adsorption, platelet activation, thrombosis, cellular adhesion, or other mechanism contributing to venous occlusion. The ethylene-glycol surface modification is optionally prepared by halogenating the outer surface 68 and plasma grafting polyethylene glycol (PEG) or by immobilizing polyethylene oxide (PEO) onto the halogenated outer surface 68 via Williamson ether synthesis, for example. Some acceptable plasma grafting techniques are described in Park, K. D., Kim, Y. S., Han, D. K., Kim, Y. H., Lee, E. H. B., Suh, H. & Choi, K. S. (1998) Biomaterials 19, pp. 851-859, the contents of which are incorporated herein by reference.

In some embodiments, the outer surface 68 includes SIBS, PDMS, and/or PU material, for example, and the surface treatment 80 includes a surface modification of fluorinated hydrocarbon implantation to provide at least one of reduced protein adsorption, platelet activation, cellular adhesion, thrombus formation, or other mechanism contributing to venous occlusion. For example, the surface modification optionally includes utilizing fluorocarbon deposition techniques such as those described in U.S. Pat. No. 5,091,204, entitled "Polymeric Intraocular Lens Material Having Improved Surface Properties," issued Feb. 25, 1992 and Ruardij, T. G., Goedbloed, M. H. & Rutten, Wim L. C. (December 2000) IEEE Transactions on Biomedical Engineering, Vol. 47, No. 12, the contents of each of which are incorporated herein by reference.

In some embodiments, the outer surface 68 includes SIBS, PDMS, and/or PU material, for example, and the surface treatment 80 includes a surface modification of phosphorylcholine grafted to a chemical backbone of the material to provide at least one of reduced protein adsorption, platelet activation, cellular adhesion, and thrombus formation. Acceptable grafting techniques are described in Jung-Sook Bae, Eun-Jin Seo, & Inn-Kyu Kang (1999) Biomaterials 20, pp. 529-537, the contents of which are incorporated herein by reference. In related embodiments, the surface modification is provided by dip-coating, plasma grafting, or cross-linking methacrylated phosphorylcholine (MPC) onto the material of the outer surface 68.

In some embodiments, the outer surface 68 includes SIBS, PDMS, and/or PU material, for example, and the surface treatment 80 includes a surface modification of heparin grafting on the material. For example, the material is optionally oxygen plasma treated, immersed in dry acetonitrile containing acrylic acid (AA) and/or methyl acrylate (MA) at an appropriate temperature and time, washed with an aqueous solution to remove any free homopolymer that has formed, further washed with distilled water, and dried under reduced pressure. 1-Ethyl-3-dimethyl amidopropyl carbodiimide (WSC) is dissolved in a sodium citrate aqueous solution and the material of the outer surface 68 is immersed in the WSC aqueous solution for a few hours to activate carboxyl groups formed on the material. The material is washed with double distilled water and incubated in an aqueous solution containing amino-terminated polyethylene oxide (PEO) at a suitable temperature, pH, and time to obtain surface grafted PEO.

In some embodiments, in order to keep a free amino group at one end of the PEO after the reaction, an excessive amount of PEO is used in the coupling reaction with the carboxylic acid surface groups. Carboxyl groups of heparin are optionally activated by the direct method using WSC or by the activation method using N-hydroxysuccinimide and dicyclohexyl carbodiimide, for example. The carboxylated material of the outer surface 68 is then immersed in a sodium citrate solution containing heparin that is previously activated with WSC, and maintained at a suitable temperature and pH for about 24 hours to obtain immobilized heparin. After the immobilization reaction, the material is thoroughly washed with DI water. Acceptable techniques for grafting heparin are described in Jung-Sook Bae, Eun-Jin Seo, & Inn-Kyu Kang (1999) Biomaterials 20, pp. 529-537, the contents of which are incorporated herein by reference.

In some embodiments, the outer surface 68 includes SIBS, PDMS, and/or PU material, for example, and the surface treatment 80 includes a surface modification of grafting sulfobetaine-type zwitterions onto the material of the outer surface 68 to provide reduced venous occlusion via hemocompatibility. For example, sulfobetaine is optionally grafted according to several steps, including reacting toluene, HDI and di-butyl tin dilaurate (DBTDL) under nitrogen and immersing the outer surface material into the reactive solution. The material is then rinsed with dry toluene before immersion in a toluene solution containing dimethyl aminobutanol (DMAB). After this reaction, the material is washed with dry toluene and immersed in a toluene solution containing propane sultone (PS). Acceptable techniques for grafting sulfobetaine-type zwitterions are described in J. Yuan, J. Zhang, J. Zhu, J. Shen, S. C. Lin, W. Zhu & J. L. Fang, (October 2003), Journal of Biomaterials Applications, vol. 18, p. 123, the contents of which are incorporated herein by reference. For reference, various zwiterrion-type, non-eluting surface modifications, where zwiterrion includes a monomeric or oligomeric derivative of phosphorylcholine, taurine, or sulfobetaine, for example, are also contemplated.

The surface treatment 80 additionally or alternatively includes one or more eluting or non-eluting coatings of therapeutic agents or drugs acting as antithrombogenic, antiproliferative, anti-fibrosis and/or anti-inflammatory agents. For example, a coating of one or more of paclitaxel-SIBS, salicylic acid based polyanhydrides, sirolimus, everolimus, doxorubicin, mitomycin, fluorodeoxyuridine, heparin and its derivatives, salicylic acid and its polyahydrides, or other drug coating is provided according to some embodiments.

Although various surface modifications and coatings are described in the foregoing paragraphs, it should be understood that any variety of surface modifications and coatings adapted to reduce venous occlusion following transvenous implantation of the cardiac lead 14 are contemplated. Furthermore, it should be noted that in some embodiments, one or more surface modifications and/or coatings are combined to provide the cardiac lead surface treatment 80, including those previously described.

In some embodiments, the expansion module 12 includes a first expansion member 82 and a second expansion member 84. According to one embodiment, the first and second expansion members 82, 84 are substantially similar. In some embodiments, each of the first and second expansion members 82, 84 is a stent or stent-like device adapted to expand in diameter from a collapsed state to an expanded state to contact and mechanically support a vessel wall in the target region 78. The first and second expansion members 82, 84 are optionally self-expanding or expandable utilizing a balloon catheter, for example, as will be described in greater detail below. In general terms, the expansion module 12 is adapted to provide mechanical and/or pharmacological mechanisms for reducing venous occlusion, and in particular at the target region 78. As shown in FIG. 2, the first expansion member 82 is adapted to expand against the left brachiocephalic vein 46 adjacent the left external jugular vein 38 while the second expansion member 84 is adapted to expand against the left subclavian vein 34 adjacent the left external jugular vein 38.

In some embodiments, the first expansion member 82 includes a body 86 and an internal sleeve 88. The body 86 is optionally formed as a wire-mesh framework, for example of NiTi or other suitable material. In other embodiments, the body 86 is formed of a bioresorbable material. According to one embodiment, the body 86 includes a surface treatment, such as a surface modification or a coating of an antithrombogenic, antiproliferative, or anti-inflammatory agent to reduce one or more of cellular adhesion, proliferation, or thrombosis. For example, the body 86 is optionally provided with one or more of the eluting or non-eluting coatings and/or surface modifications such as those described in association with the cardiac lead 14.

The internal sleeve 88 is optionally a layer of material maintained within the body 86, such as a stent graft. For example, according to one embodiment, the internal sleeve 88 is a layer of hollow, tubular material residing within and expandable with the body 86. In some embodiments, the internal sleeve 88 is formed of one or more of the materials described in association with the outer surface 68 of the cardiac lead 14, such as SIBS, PU, PDMS, or ePTFE. The internal sleeve 88 optionally includes one or more surface treatments, including the surface modifications and surface coatings described in association with the outer surface 68. In some embodiments, the internal sleeve 88 reduces cellular adhesion between the cardiac lead 14 and vessel walls as well as the first expansion member 82. The internal sleeve 88 also optionally acts as a barrier to reduce cellular adhesion between the cardiac lead 14 and vessel walls surrounding the first expansion member 82.

In some embodiments, the second expansion member 84 also includes a body 90 and an internal sleeve 92 including features such as those described in association with the body 86 and internal sleeve 88 of the first expansion member 82. In some embodiments, a single expansion member is employed in the target region 78. For example, the first expansion member 82 optionally extends from the portion of the left brachiocephalic vein 46 adjacent the left external jugular vein 38 to the portion of the left subclavian vein 34 adjacent to the left external jugular vein 38.

Various systems and methods are contemplated for transvenous implantation of the cardiac lead 14 and the expansion module 12. In some embodiments, the cardiac lead 14 is transvenously implanted in the absence of the expansion module 12. In other embodiments, the expansion module 12 is implanted prior to implantation of the cardiac lead 14 or substantially concurrently with implantation of the cardiac lead 14. According to one technique, the expansion module 12 is typically applied as a prophylactic or preventative measure, prior to venous occlusion/stenosis and either as a part of, or prior to, transvenous implantation of the cardiac lead 14, although other applications are contemplated.

Figure 3:
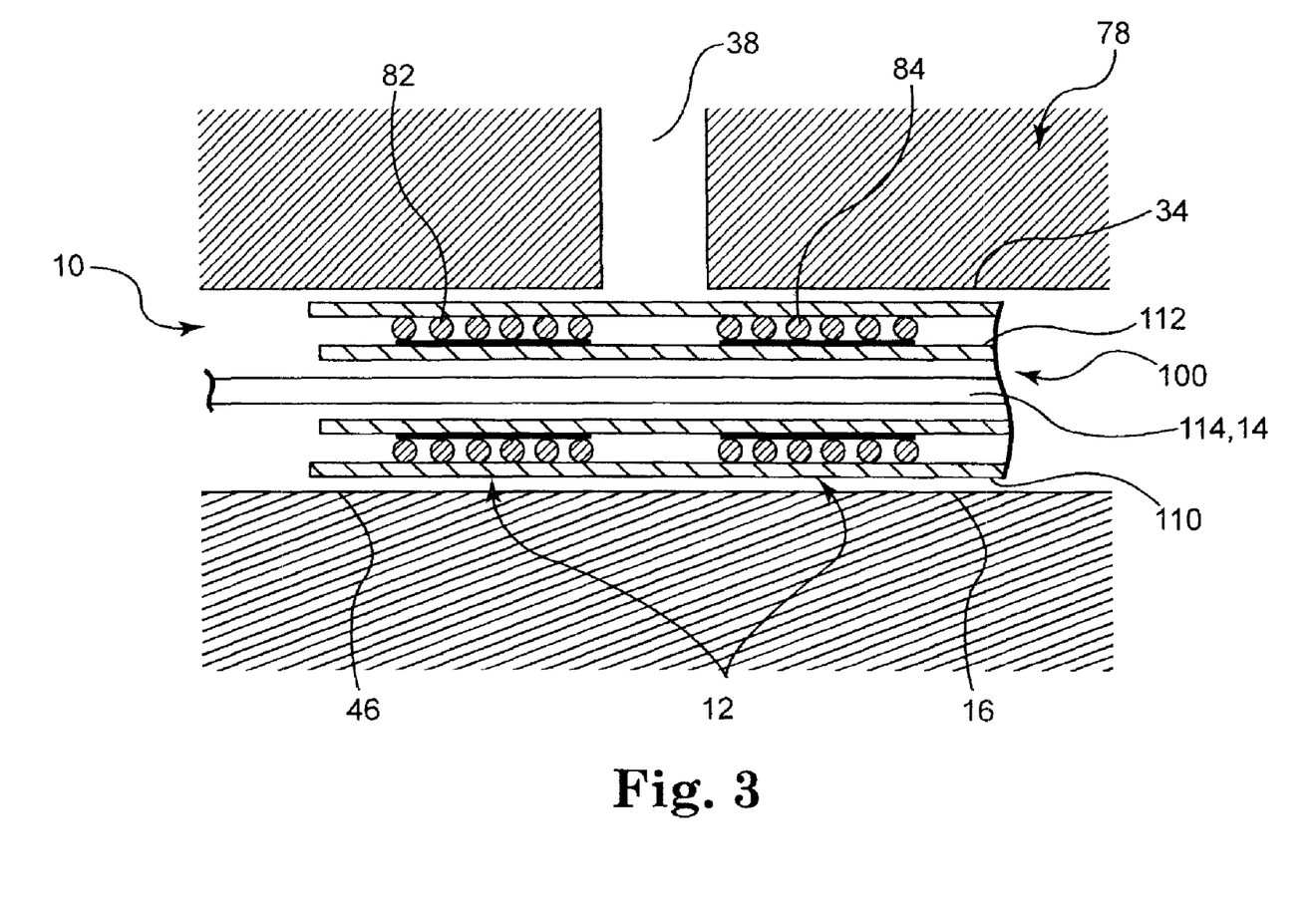
FIGS. 3-5 show a lead deployment assembly in various stages of deployment.

As shown in FIG. 3, the cardiac lead system 10 includes a deployment assembly 100 for transvenously implanting the expansion module 12 and/or cardiac lead 14 within the target region 78 (shown in a more generalized, schematic form in FIG. 3). As shown, the deployment assembly 100 includes a retractable outer sheath 110, a carrier sheath 112, and a guide body 114, where the guide body 114 is optionally a guide wire, the cardiac lead 14, or other suitable structure. The deployment assembly 100 is adapted for deploying the expansion module 12 where the first and second expansion members 82, 84 are self-expanding. However, in other embodiments, the deployment assembly 100 includes suitable expansion devices, such as a balloon catheter.

The outer sheath 110 and the carrier sheath 112 are adapted such that the carrier sheath 112 is slidably received within the outer sheath 110. Each of the outer and carrier sheaths 110, 112 is optionally a catheter, or is catheter-like, and is introducible into the vascular pathway 16, for example over a guide wire (not shown). The carrier sheath 112 is adapted to receive the cardiac lead 14 and to maintain the expansion module 12. In particular, one or both of the first and second expansion members 82, 84 are coaxially received over the carrier sheath 112, with each of the first and second expansion members 82, 84 in the collapsed state. The outer sheath 110 is disposed over the first and second expansion members 82, 84 such that the outer sheath 110 is able to be slidably retracted from the first and second expansion members 82, 84.

The outer sheath 110 is able to be slid back from the first and second expansion members 82, 84 such that they self-expand at a deployment site, for example within the target region 78 as previously described. In some embodiments, the cardiac lead 14 serves as the "carrier sheath" with the first and second expansion members 82, 84 directly loaded onto the cardiac lead 14 and held in the collapsed state by the outer sheath 110. Then, in a similar manner to that previously described, the outer sheath 110 is slid back from the first and second expansion members 82, 84 allowing the first and second expansion members 82, 84 to expand against the surrounding vessel walls as desired.

In still other embodiments, the first and second expansion members 82, 84 are deployed in series, via catheters or other devices used for deploying self-expanding stents or the like at a desired deployment site. Furthermore, other embodiments include utilizing balloon catheters or other devices for deploying and expanding one or both of the first and second expansion members 82, 84 at a desired deployment site.

Various methods of deploying a transvenous lead system are subsequently described with reference to FIGS. 3-5. While various embodiments are generally described in association with the left side of the body, similar principles apply to the right side of the body, as well as alternate vascular pathways to the vascular pathway 16. In some embodiments, a surgeon or other user (not shown) gains access to the vascular pathway 16 through left axillary vein 30 or the left subclavian vein 34. An introducer sheath (not shown) and the guide body 114 are introduced into the vascular pathway 16. The carrier sheath 112 and the outer sheath 110 are slid into the vascular pathway 16 over the guide body 114 with the expansion module 12 maintained on the carrier sheath 112.

The expansion module 12 is optionally located at a desired deployment site, for example the target region 78, under fluoroscopy or using other imaging techniques. In some embodiments, the first expansion member 82 is disposed in the left brachiocephalic vein 46 adjacent the left external jugular vein 38 as shown in FIG. 3. In turn, the second expansion member 84 is disposed in the left subclavian vein 34 adjacent the left external jugular vein 38. Although FIG. 3 generally shows the first and second expansion members 82, 84 disposed at the deployment site as part of a single process, it should be understood that the first and second expansion members 82, 84 are optionally deployed in a series, for example using other devices and techniques for deploying stents or stent-like structures.

In some embodiments, the cardiac lead 14 serves as the guide body 114. In this manner, proper positioning of the first and second expansion members 82, 84, at the target region 78 for example, also helps ensure proper positioning of the intermediate section 72 in the target region 78, and vice versa. In other words, the first and second expansion members 82, 84 are optionally viewed under fluoroscopy during positioning thereof, which, in turn, also facilitates proper positioning of the cardiac lead 14 with the intermediate section 72 at the target region 78. In other embodiments, the guide body 114 is a guide wire and the cardiac lead 14, or a plurality of cardiac leads, are subsequently deployed over the guide body 114 as desired. For example, the cardiac lead 14 is optionally subsequently deployed over the guide body 114 after the expansion module 12 has been deployed.

Figure 4:
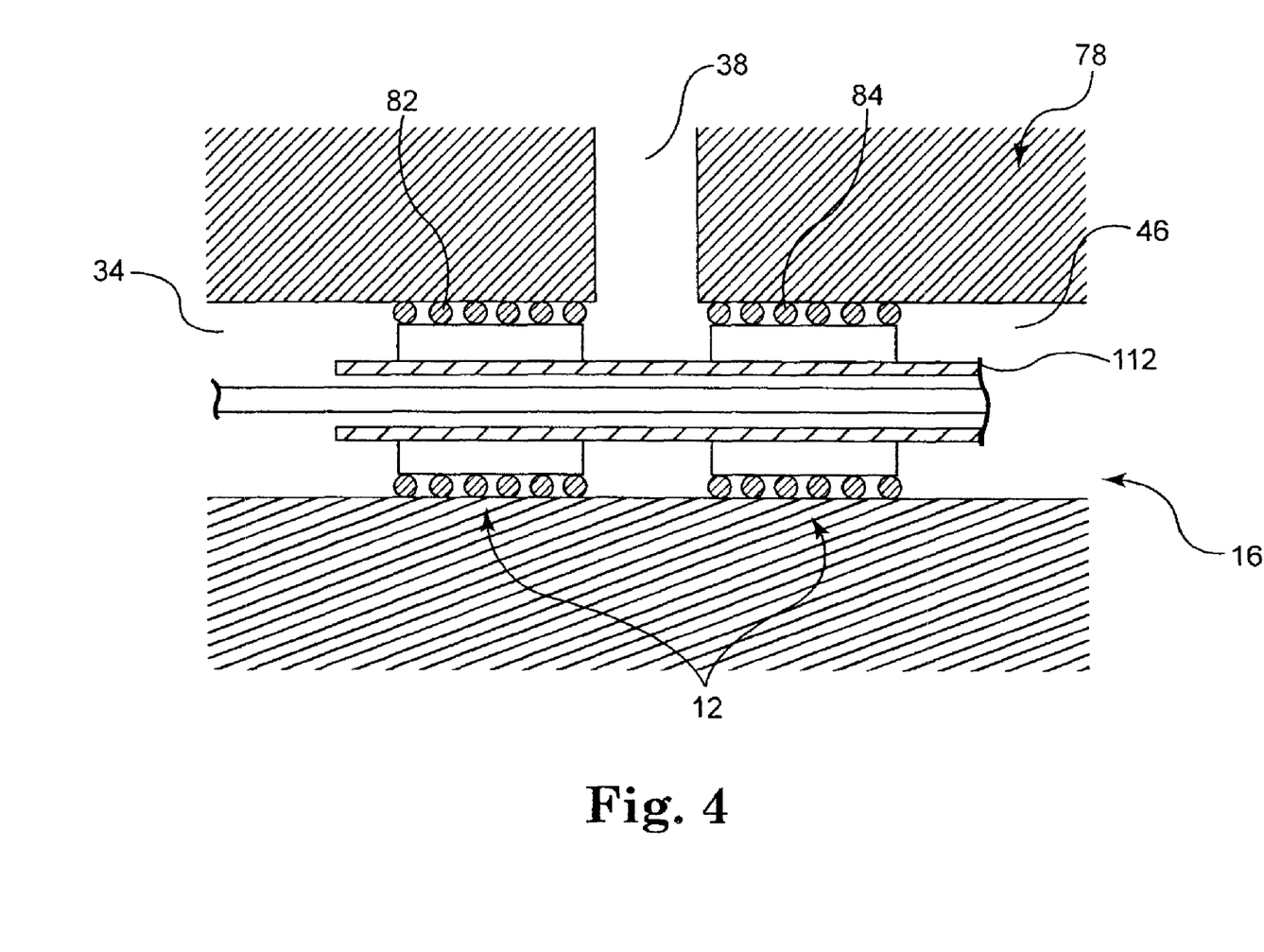

As shown in FIG. 4, once the expansion module 12 is disposed at the deployment site within the vascular pathway 16, the outer sheath 110 (FIG. 3) is retracted from the first and second expansion members 82, 84, respectively, to allow each of the first and second expansion members 82, 84 to expand against the venous walls at the deployment site, for example the left brachiocephalic vein 46 and the left subclavian vein 34 in the target region 78.

Figure 5:
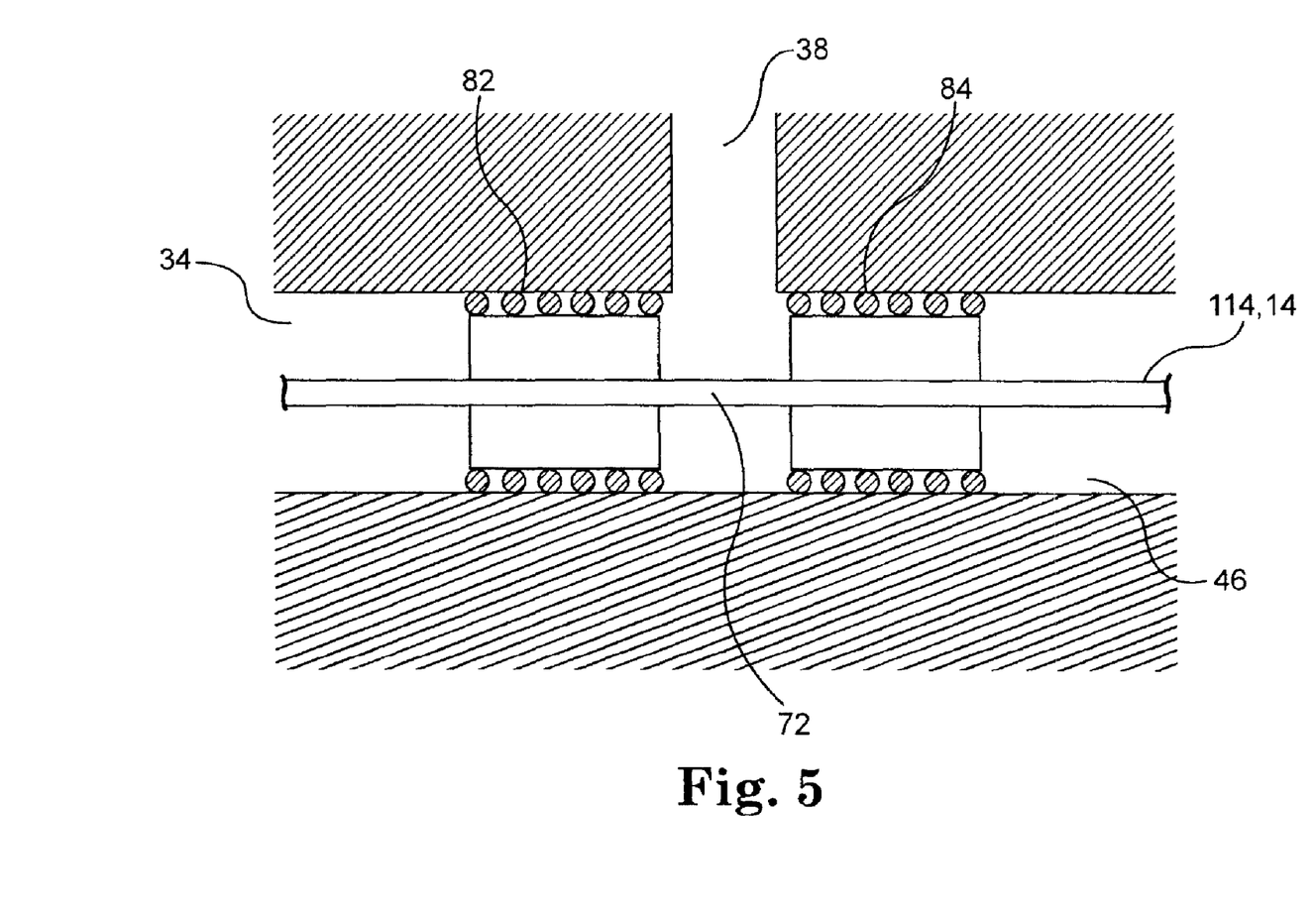

As shown in FIG. 5, the carrier sheath 112 (FIG. 4) is then retracted with the cardiac lead 14 slidably received within the expansion module 12. In some embodiments, the first and second expansion members 82, 84 remain in the vascular pathway 16 following implantation. In other embodiments, the first and second expansion members 82, 84 or portions thereof, for example the bodies 86, 90, are bioresorbable into the vascular walls, for example.

Figure 6:
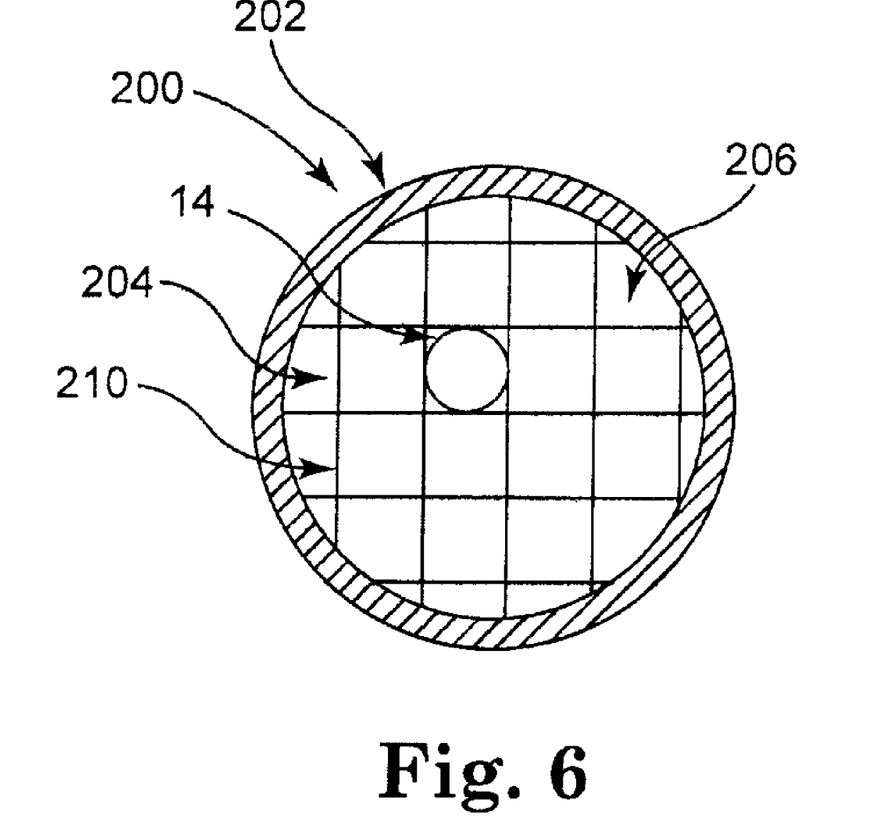
FIG. 6 is a cross-sectional view of an expansion member according to an exemplary embodiment.

FIG. 6 is a cross-sectional view of another exemplary embodiment expansion member 200 including an expandable body 202 and an internal guide structure 204. The expandable body 202 defines an inner lumen 206 and is optionally substantially similar to the first or second expansion members 82, 84. In one exemplary embodiment, the internal guide structure 204 comprises a series of filaments 210 secured to the expandable body 202. As shown, the filaments 210 define a grid pattern or framework for supporting an implanted device, such as the cardiac lead 14 at a desired radial position within the inner lumen 206, for example substantially centered, or coaxially, within the inner lumen 206. The internal guide structure 204 would, for example, be used to reduce contact between the cardiac lead 14 and a vessel wall (or other leads) while allowing blood to flow through the expansion member 200.

The preceding description provides systems, methods, and devices for reducing venous at targeted regions within a vascular pathway, such as the target region 78. For example, the provision of surface treatments associated with the expansion module 12 and/or the cardiac lead 14 optionally assists with occlusion reduction. The antithrombogenic, antiproliferative, anti-fibrosis, anti-inflammatory, and other occlusion reducing surface treatments provide for improved systems and methods for transvenous lead implantation, including reduced venous occlusion and lead attachment associated with transvenously implanted leads. Additionally, by implanting the expansion module 12 proactively as a prophylactic measure prior to the onset of venous occlusion, difficulties associated with removing leads and later implanting therapeutic devices may be avoided. As another example, the expansion module 12 is adapted to facilitate reduced cellular adhesion between the cardiac lead 14 and vessel walls, which, in turn, facilitates removal of the cardiac lead 14 for maintenance or replacement, and can also serve to reduce venous occlusion mechanisms, such as irritation and cell proliferation at the various interfaces between the cardiac lead 14, expansion module 12, and vessel wall interfaces, respectively.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of implanting a cardiac lead, the method comprising:
   implanting an expansion module in a target region within vasculature, the target region being defined by a portion of a brachiocephalic vein and a portion of a corresponding subclavian vein;
   transitioning the expansion module from a collapsed state to an expanded state within the target region to contact the vasculature; and
   implanting a cardiac lead through the expansion module, the cardiac lead defining an intermediate section corresponding to the target region;
   wherein the intermediate section of the cardiac lead includes a surface treatment adapted to reduce at least one of cell proliferation, thrombosis, fibrosis, and inflammation at the target region.

2. The method of claim 1, wherein the surface treatment of the intermediate section includes a non-eluting surface modification selected from the group consisting of: a polyethylene-glycol surface modification, ethylene-glycol surface modification, a fluorinated hydrocarbon surface modification, a phosphorylcholine surface modification, a taurine surface modification, a sulfobetaine surface modification, a zwitterion-type surface modification, and combinations thereof.

3. The method of claim 1, wherein the surface treatment of the intermediate section includes an eluting coating of a therapeutic agent selected from the group consisting of: paclitaxel-SIBS, salicylic acid based polyanhydrides, sirolimus, everolimus, doxorubicin, mitomycin, fluorodeoxyuridine, heparin, heparin derivatives, salicylic acid, salicylic acid polyahydrides, and combinations thereof.

4. The method of claim 1, wherein the expansion module includes at least one of an internal sleeve adapted to reduce cellular adhesion between the intermediate section of the cardiac lead and the vasculature and a surface modification adapted to reduce venous occlusion at the target region.

5. The method of claim 1, wherein the brachiocephalic, external jugular, and subclavian veins correspond to the left side of the body.

6. A method of implanting a cardiac lead prior to venous occlusion at a target region defined by a junction of a brachiocephalic vein and an external jugular vein, the method comprising:
   implanting a first expansion member in a vascular pathway including the target region;
   expanding the first expansion member to an expanded state in the target region; and
   implanting a cardiac lead within the vascular pathway such that the cardiac lead extends through the target region and is received within the first expansion member, the cardiac lead including an insulator defining an outer surface of the cardiac lead;
   wherein at least a portion of the outer surface of the cardiac lead extending through the target region includes a non-eluting surface modification including at least one of a polyethylene-glycol surface modification, an ethylene-glycol surface modification, a fluorinated hydrocarbon surface modification, a phosphorylcholine surface modification, a taurine surface modification, a sulfobetaine surface modification, and a zwitterion-type surface modification.

7. The method of claim 6, wherein at least one of the first and second expansion members includes an internal sleeve having a non-eluting surface modification.

8. The method of claim 7, wherein the internal sleeve is formed of ePTFE.

9. The method of claim 6, wherein the first expansion member further comprises an internal guide structure supporting the cardiac lead at a desired radial position within the first expansion member.

* * * * *